(12) United States Patent
Yu et al.

(10) Patent No.: US 9,823,312 B2
(45) Date of Patent: Nov. 21, 2017

(54) APPARATUS AND METHOD FOR INDIRECTLY COOLING SUPERCONDUCTING QUANTUM INTERFERENCE DEVICE

(71) Applicant: Korea Research Institute of Standards and Science, Daejeon (KR)

(72) Inventors: Kwon-Kyu Yu, Daejeon (KR); Yong-Ho Lee, Daejeon (KR); Kiwoong Kim, Daejeon (KR); Hyukchan Kwon, Daejeon (KR); Jin-Mok Kim, Daejeon (KR); Sang-Kil Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 374 days.

(21) Appl. No.: 14/692,258

(22) Filed: Apr. 21, 2015

(65) Prior Publication Data

US 2015/0268311 A1  Sep. 24, 2015

Related U.S. Application Data

(63) Continuation of application No. PCT/KR2013/009105, filed on Oct. 11, 2013.

(30) Foreign Application Priority Data

Oct. 29, 2012  (KR) .................. 10-2012-0120366

(51) Int. Cl.
*F28F 7/00* (2006.01)
*G01R 33/00* (2006.01)
(Continued)

(52) U.S. Cl.
CPC .............. *G01R 33/007* (2013.01); *A61B 5/05* (2013.01); *G01R 1/18* (2013.01); *G01R 33/035* (2013.01);
(Continued)

(58) Field of Classification Search
CPC .... G01R 33/007; G01R 33/0035; G01R 1/18; G01R 33/0354; H01L 23/367;
(Continued)

(56) References Cited

U.S. PATENT DOCUMENTS 4,827,217 A * 5/1989 Paulson ............. A61B 5/04005
324/201
5,441,107 A * 8/1995 Esser ................. G01R 33/0358
165/185

(Continued)

FOREIGN PATENT DOCUMENTS

| JP | 5251774 | 9/1993 |
| JP | 3867158 B2 | 1/2007 |
| KR | 10 2002 0036784 A | 5/2002 |

OTHER PUBLICATIONS

English Translation of the International Search Report with IPRP and Written Opinion for Application No. PCT/KR2013/009105 dated May 5, 2015.

*Primary Examiner* — Len Tran
*Assistant Examiner* — Claire Rojohn, III
(74) *Attorney, Agent, or Firm* — Jenkins, Wilson, Taylor & Hunt, P.A.

(57) ABSTRACT

An apparatus and a method for indirectly cooling a superconducting quantum interference device (SQUID) are provided. The apparatus includes an outer container extending in a vertical direction; a metallic inner container inserted into the outer container to store a liquid coolant, the metal inner container including a top plate; a SQUID sensor module disposed between a bottom surface of the outer container and a bottom surface of the inner container; a heat transfer pillar adapted to cool the SQUID sensor module, the heat transfer pillar having one end connected to the bottom surface of the inner container and the other end directly or indirectly connected to the SQUID sensor module; a mag- (Continued)

netic shield part formed of a superconductor covering a top surface of the SQUID sensor module; and a heat conduction plate being in thermal contact with the other end of the heat transfer pillar.

15 Claims, 3 Drawing Sheets

(51) Int. Cl.
    *A61B 5/05*     (2006.01)
    *G01R 33/035*     (2006.01)
    *G01R 1/18*     (2006.01)
    *H01L 23/367*     (2006.01)
    *H01L 23/473*     (2006.01)
    *H01L 39/02*     (2006.01)
    *A61B 5/04*     (2006.01)

(52) U.S. Cl.
    CPC ........ *G01R 33/0354* (2013.01); *H01L 23/367* (2013.01); *H01L 23/473* (2013.01); *H01L 39/02* (2013.01); *A61B 5/04005* (2013.01); *H01L 2924/0002* (2013.01)

(58) Field of Classification Search
    CPC .................. H01L 23/473; H01L 39/02; H01L 2924/0002; A61B 55/05; A61B 5/04005
    USPC ........................................................ 165/138
    See application file for complete search history.

(56) References Cited

U.S. PATENT DOCUMENTS

| | | | |
|---|---|---|---|
| 5,834,938 A * | 11/1998 | Odawara | G01R 33/035 324/224 |
| 6,332,324 B1 | 12/2001 | Saho et al. | |
| 2002/0153884 A1 * | 10/2002 | Nagaishi | G01R 33/0354 324/248 |
| 2009/0146232 A1 * | 6/2009 | Wunderlich | B82Y 25/00 257/421 |
| 2015/0226813 A1 * | 8/2015 | Yu | A61B 5/05 324/224 |

* cited by examiner

APPARATUS AND METHOD FOR INDIRECTLY COOLING SUPERCONDUCTING QUANTUM INTERFERENCE DEVICE

CROSS-REFERENCE TO RELATED APPLICATIONS

This application is a continuation of and claims priority to PCT/KR2013/009105 filed on Oct. 11, 2013, which claims priority to Korea Patent Application No. 10-2012-0120366 filed on Oct. 29, 2012, the entireties of which are hereby incorporated by reference herein.

BACKGROUND

1. Technical

The present disclosure relates generally to apparatuses for cooling a superconducting quantum interference device and, more particularly, to apparatuses for indirectly cooling a superconducting quantum interference device.

2. Description of the Related Art

A superconducting quantum interference device (hereinafter referred to as "SQUID") is an ultrasensitive sensor which is capable of measuring a hyperfine magnetic field generated in biological activities of heart, brain, muscles, and the like. A SQUID sensor operates at extremely low temperature of 4K or 77K. Measurement sensitivity is several to tens of fT/√Hz. In general, liquid nitrogen or liquid helium is used to cool the SQUID sensor to low temperature. A low-temperature coolant storage container is required to store such a low-temperature coolant.

SUMMARY

Embodiments of the present disclosure provide a low-temperature coolant storage container for measuring biomagnetism which uses a metallic material instead of G-10 epoxy.

Embodiments of the present disclosure provide a stable operation of a system by protecting a SQUID sensor from thermal noise and magnetic noise generated from a metallic material using a superconducting shield.

An apparatus for indirectly cooling a superconducting quantum interference device (SQUID) according to an embodiment of the present disclosure may include an outer container extending in a vertical direction; a metallic inner container inserted into the outer container to store a liquid coolant, the metal inner container including a top plate; a SQUID sensor module disposed between a bottom surface of the outer container and a bottom surface of the inner container; a heat transfer pillar adapted to cool the SQUID sensor module, the heat transfer pillar having one end connected to the bottom surface of the inner container and the other end directly or indirectly connected to the SQUID sensor module; a magnetic shield part formed of a superconductor covering a top surface of the SQUID sensor module; and a heat conduction plate being in thermal contact with the other end of the heat transfer pillar, the heat conduction plate being stacked on a top surface of the magnetic shield part. The inner container may have a space spaced apart from the outer container, and a space between the inner container and the outer container may be in a vacuum state.

In an example embodiment, the apparatus may further include an auxiliary heat transfer layer disposed to a bottom surface of the SQUID sensor module.

In an example embodiment, the auxiliary heat transfer layer may be formed of a copper mesh, and wefts and warps of the copper mesh may be electrically insulated from each other.

In an example embodiment, the auxiliary heat transfer layer may include an epoxy layer; and copper conductors stacked on the epoxy layer and extending parallel with each other at regular intervals.

In an example embodiment, the apparatus may further include a fixing ring formed of a conductor to fix the auxiliary heat transfer layer to the bottom surface of the inner container.

In an example embodiment, the apparatus may further include a fixing block formed of a copper material and fixed to the bottom surface of the inner container to transfer heat to the heat transfer pillar.

In an example embodiment, the outer container may include an upper outer cylinder; a washer-shaped outer middle plate connected to a bottom surface of the upper outer cylinder; a lower outer cylinder being in contact with an inner side surface of the outer middle plate to vertically extend; and an outer base plate disposed on a bottom surface of the lower outer cylinder.

In an example embodiment, the inner container may include a neck portion connected to an inner side surface of a through-hole formed in the center of a top plate, the neck portion extending vertically; a washer-shaped inner middle plate connected to a bottom surface of the neck portion, the inner middle plate having a through-hole in its center; a cylindrical inner body portion extending vertically from an outer side surface of the inner middle plate; and an inner base plate disposed on a bottom surface of the inner body portion.

In an example embodiment, the SQUID sensor module may include a sensor coupling plate formed of a dielectric material; sensor fixing blocks mounted on a bottom surface of the sensor coupling plate; and SQUID sensors coupled with the sensor fixing blocks.

In an example embodiment, the magnetic shield part may be formed of lead (Pb) or niobium (Nb).

In an example embodiment, the heat conduction plate and the heat transfer pillar may be formed of an oxygen-free copper material.

In an example embodiment, the magnetic shield part may extend vertically to cover the SQUID sensor module.

In an example embodiment, the apparatus may further include a first support plate coupled with an outer side surface of the inner container, the first support plate having a first diameter and including a first conductive thermal anchor formed on its outer circumferential surface; a second support plate spaced vertically apart from the first support plate to be coupled with the outer side surface of the inner container, the second support plate having a second diameter smaller than the first diameter and including a second conductive thermal anchor formed on its outer circumferential surface; a third support plate spaced vertically apart from the second support plate to be coupled with the outer side surface of the inner container, the second support plate having a third diameter smaller than the second diameter and including a third conductive thermal anchor formed on its outer circumferential surface; a first thermal shield part coupled with the first thermal anchor and extending vertically; a second thermal shield part coupled with the second thermal anchor and extending vertically; and a third thermal shield part coupled with the third thermal anchor and extending vertically.

A method for indirectly cooling a superconducting quantum interference device (SQUID) according to an embodiment of the present disclosure may include providing an outer container extending vertically and a metallic inner container inserted into the outer container to store a liquid coolant, the inner container including a top plate and a space between the inner container and the outer container being in a vacuum state; providing a SQUID sensor module between a bottom surface of the outer container and a bottom surface of the inner container; providing a heat transfer pillar having one end connected to the bottom surface of the inner container and the other end connected directly or indirectly to the SQUID sensor module to cool the SQUID sensor module; providing a magnetic shield with a superconductor disposed to cover a portion of the SQUID sensor module; and providing a heat conduction plate being in thermal contract with the other end of the heat transfer pillar and being adapted to cool the superconductor.

In an example embodiment, the method may further include providing an auxiliary heat transfer layer covering a bottom surface of the SQUID sensor module to cool the heat transfer pillar, the superconductor, and the SQUID sensor module.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

A low-temperature coolant storage container is formed of a nonmagnetic material that has magnetic properties for the stable operation of a SQUID sensor without distorting a magnetic field generated from a living body. In addition, a material of very low heat conductivity is used to minimize an evaporation rate of liquid nitrogen or liquid helium used as a coolant of the SQUID sensor.

In general, glass fiber reinforced epoxy is used and called G-10 epoxy. The G-10 epoxy is used as a material of a low-temperature storage container for measuring biomagnetism.

A low-temperature coolant storage container includes an outer container and an inner container. The outer container and the inner container have a hollow tube shape using the G-10 epoxy. The inner container is inserted into the outer container, and a space between the outer container and the inner container is maintained at a vacuum state.

Conventionally, a structure of a low-temperature coolant storage container for reducing an evaporation rate of a liquid coolant has a three-fold thermal shield. The thermal shield decreases a temperature gradient. In addition, a superinsulation layer is disposed between thermal shields to block radiant heat influx. Thirty sheets of superinsulator and thirty sheets of polyester net, total 100 folds or more are mounted on the superinsulation layer.

Conventionally, the inner container may be divided into a neck portion and a main reservoir. A vacuum layer is formed between the inner container and the outer container to prevent heat conduction to the outside from the main reservoir to store a low-temperature coolant. A G-10 epoxy tube and a G-10 epoxy plate constituting the low-temperature coolant storage container are bonded using an epoxy adhesive after being processed.

In general, a conventional SQUID sensor module is inserted into a low-temperature coolant to be directly cooled. In case of such as direct cooling method, an insert and the SQUID sensor module are inserted through the neck portion of the inner container. The SQUID sensor module is coupled with the end of the insert. A diameter of the neck portion of the inner container may be large enough to insert the SQUID sensor module. The SQUID sensor module is affected by vibration noise and heat influx via the insert. The vibration noise decreases operation stability and a signal-to-noise (SNR) of the SQUID sensor module, and the heat influx increases an evaporation rate of a coolant.

In order to overcome the above disadvantages, there was developed an indirect cooling technique in which a SQUID sensor is not directly cooled using a coolant but the SQUID sensor is disposed at the vacuum layer.

However, a material used for heat transfer in a conventional indirect cooling technique has a superior heat transfer characteristic but must be a non-metal material. Conventionally, alumina ($Al_2O_3$) processed in the form of a rod is used as a heat transfer material. Alternatively, a G-10 epoxy rod into which a thin copper (Cu) wire is inserted is used as a heat transfer material.

A material of a low-temperature coolant storage device for use in a SQUID for measuring biomagnetism must be low in heat conductivity and very low in deformation with respect to temperature change. In addition, a material of the low-temperature coolant storage device must be a non-metal material that does not distort a magnetic signal generated by biological activity.

A generally used material is a glass fiber reinforced epoxy tube. The glass fiber reinforced epoxy tube is very limited in use and processing due to harmfulness of a glass fiber and high toxicity of an epoxy resin. An epoxy-resin-containing material has higher shrinkage than a metal according to temperature variation. The epoxy-resin-containing material causes a gas produced by evaporating a liquid coolant (liquid nitrogen, liquid helium, etc.) to transmit the vacuum layer, which is called "softening phenomenon". Accordingly, characteristics of the low-temperature coolant storage container are degraded.

If a low-temperature coolant storage container is formed of a metal to overcome the above disadvantage, thermal noise and magnetic noise generated by the metal causes an unstable operation of a SQUID sensor. Thus, the SQUID sensor detects a biomagnetic signal distorted by a metal low-temperature coolant storage container.

Such a distorted signal causes analysis and localization of a signal source to be very inaccurate.

An embodiment of the present disclosure provides a manufacturing method for using a metal low-temperature coolant storage container (Dewar) to measure biomagnetism and a superconducting shield method for removing thermal noise and magnetic noise generated from the metal low-temperature coolant storage container (Dewar). In addition, a SQUID sensor is cooled by an indirect cooling method.

According to an embodiment of the present disclosure, the inside of a low-temperature coolant storage container of a SQUID apparatus for measuring biomagnetism is formed of a metal material and a superconducting magnetic shield is used to protect a SQUID sensor from thermal noise and magnetic noise of the metal material.

Preferred embodiments of the present disclosure will be described below in more detail with reference to the accompanying drawings. The present disclosure may, however, be embodied in different forms and should not be constructed as limited to the embodiments set forth herein. Rather, these embodiments are provided so that this disclosure will be thorough and complete, and will fully convey the scope of the present disclosure to those skilled in the art. Like numbers refer to like elements throughout.

Figure 1:
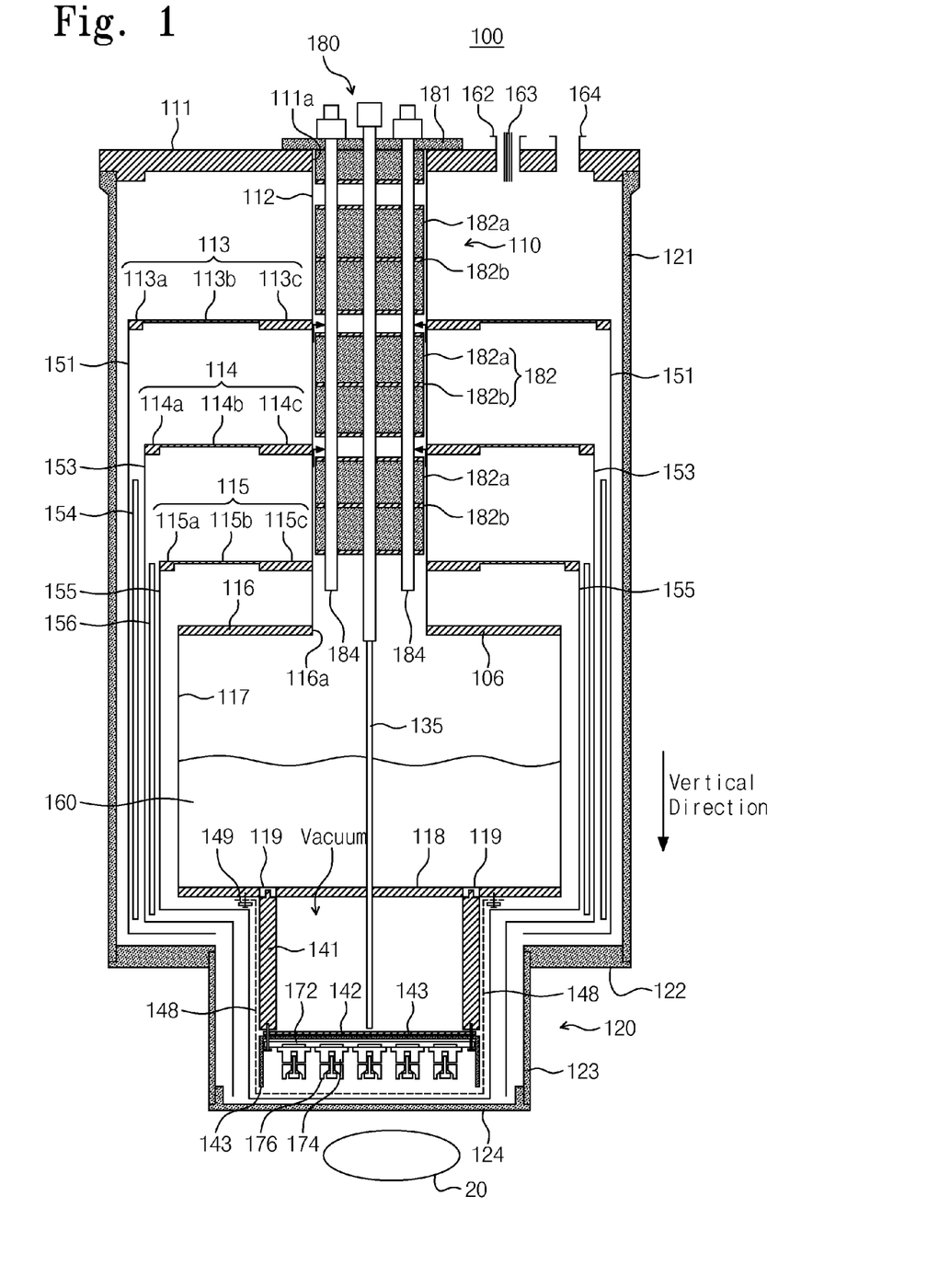
FIG. 1 is a cross-sectional view of an apparatus for indirectly cooling a superconducting quantum interference device (SQUID) according to an embodiment of the present disclosure.

FIG. 1 is a cross-sectional view of an apparatus for indirectly cooling a superconducting quantum interference device (SQUID) according to an embodiment of the present disclosure.

Figure 2:
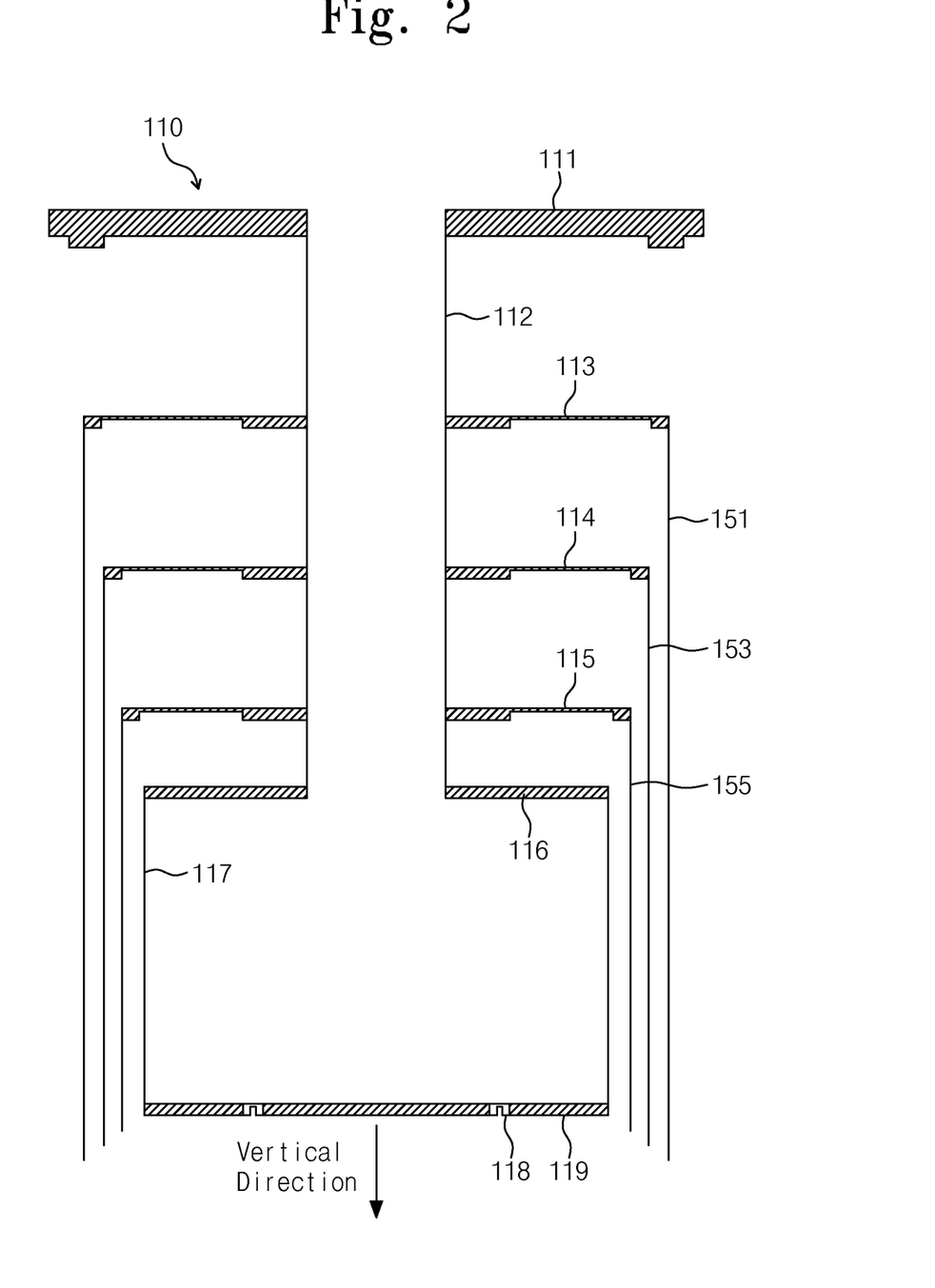
FIG. 2 is a cross-sectional view of an inner container in FIG. 1.

FIG. 2 is a cross-sectional view of an inner container in FIG. 1.

Figure 3:
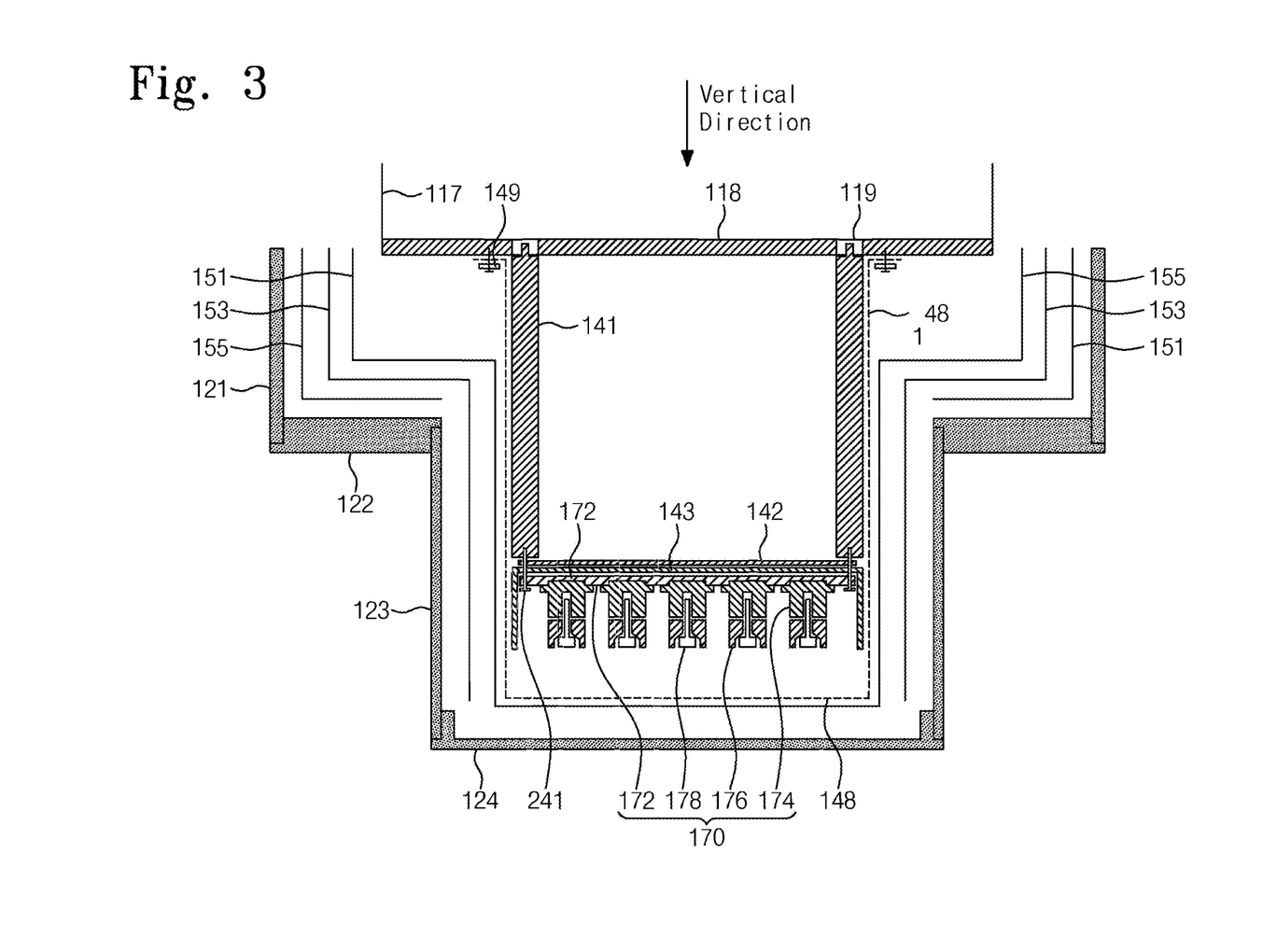
FIG. 3 is a cross-sectional view of a SQUID sensor module in FIG. 1.

FIG. 3 is a cross-sectional view of a SQUID sensor module in FIG. 1.

Referring to FIGS. 1 to 3, an apparatus 100 for indirectly cooling a superconducting quantum interference device (SQUID) includes an outer container 120 that extends in a vertical direction, a metallic inner container 110 that is inserted into the outer container 120 to store a liquid coolant and includes a top plate, a SQUID sensor module 170 disposed between a bottom surface of the outer container 120 and a bottom surface of the inner container 110, a heat transfer pillar 141 that cools the SQUID sensor module 170 and has one end connected to the bottom surface of the inner container 110 and the other end directly or indirectly connected to the SQUID sensor module 170, a magnetic shield part 142 that is formed of a superconductor covering a top surface of the SQUID sensor module 170, and a heat conduction plate 142 that is in thermal contact with the other end of the heat transfer pillar and is stacked on a top surface of the magnetic shield part. The inner container 110 has a space spaced apart from the outer container 120, and a space between the inner container 110 and the outer container 120 is a vacuum layer. The vacuum layer blocks conductive heat.

The outer container 120 includes an upper outer cylinder 121, a washer-shaped outer middle plate 122 connected to a bottom surface of the upper outer cylinder 121, a lower outer cylinder 123 being in contact with an inner side surface of the outer middle plate 122 to vertically extend, and an outer base plate 124 disposed on a bottom surface of the lower outer cylinder 123. The outer container 120 may be formed of G-10 epoxy or a metal. A first diameter of the upper outer cylinder 121 is greater than a second diameter of the lower outer cylinder 123. The outer middle plate 122 may be in the form of a washer, and the outer base plate 124 may be in the form of a circular plate. The upper outer cylinder 121 may be coupled with an outer circumferential surface of the outer middle plate 122, and the lower outer cylinder 123 may be coupled with an inner circumferential surface of the outer middle plate 122. These coupled portions may be sealed with an epoxy resin.

The inner container 110 may include a neck portion 112 that is connected to an inner side surface of a through-hole 111a formed in the center of a top plate 111 and extends vertically, a washer-shaped inner middle plate 116 that is connected to a bottom surface of the neck portion 112 and has a through-hole 116a in its center, a cylindrical inner body portion 117 that extends vertically from an outer side surface of the inner middle plate 116, and an inner base plate 118 disposed on a bottom surface of the inner body portion 117. The inner container 110 may be formed of a metal having low heat conductivity. More specifically, the inner container 110 may be formed of stainless steel. A coupled portion of the inner container 110 may be welded. A space between the inner container 110 and the outer container 120 may be a vacuum layer. The vacuum layer may block conductive heat. The inside of the body portion 117 of the inner container 110 may be filled with a coolant such as liquid nitrogen or liquid helium. The top plate 111 may include a vacuum port 164 for maintaining a vacuum state and a connection port 162 for electrical connection.

Radiation heat and conduction heat must be blocked to reduce an evaporation rate of liquid helium of absolute temperature of 4K or liquid nitrogen of absolute temperature of 77K. First to third thermal shield parts 151, 153, and 155 are disposed between the inner container 110 and the outer container 120 to block the radiation heat.

A first support plate 113 is formed of a conductive material, is coupled with an outer side surface of the neck portion 112 of the inner container 110, has a first diameter, and includes a first thermal anchor 113a formed on its outer circumferential surface. The first support plate 113 may be formed of aluminum or copper. The first support plate 113 may thermally connect the first thermal shield part 151 and the neck portion 112 to each other. The first thermal anchor 113a may be a thick portion, a first extension 113b may be a thin portion, and a first neck connection portion 113c may be a thick portion. The radiation heat absorbed by the first support plate 113 and the first thermal shield part 151 is transferred to the neck portion 112 through the first support plate 113. Accordingly, a gaseous coolant passing through the inside of the neck portion 112 receives the absorbed radiation heat.

A second support plate 114 is formed of a conductive material, is vertically spaced apart from the first support plate 113 to be coupled with an outer side surface of the neck portion 112 of the inner container 110, has a second diameter less than the first diameter, and includes a second anchor 114a formed on its outer circumferential surface. The second support plate 114 may be formed of aluminum or copper. The second anchor 114a may be a thick portion, a second extension 114b may be a thin portion, and a second neck connection portion 114c may be a thick portion.

A third support plate 115 is formed of a conductive material, is vertically spaced apart from the second support plate 114 to be coupled with the outer side surface of the neck portion 112, has a third diameter less than the second diameter, includes a third anchor 115a formed on its outer circumferential surface. The third support plate 115 may be formed of aluminum or copper. The third anchor 115a may be a thick portion, a third extension 115b may be a thin portion, and a third neck connection portion 115c may be a thick portion.

The first thermal shield part 151 may be coupled with the first thermal anchor 113a and extend vertically. The first thermal shield part 151 may have a cylindrical shape. The first thermal shield part 51 may be formed of aluminum or copper. A lower end of the first thermal shield part 151 may have a slit shape. The first to third thermal shield parts 151, 153, and 155 may reduce a temperature gradient to effectively block out the entrance of the radiation heat influx.

The second thermal shield part 153 may be coupled with the second thermal anchor 114a and extend vertically. The second thermal shield part 153 may be formed of aluminum or copper.

The third thermal shield part 155 may be coupled with the third thermal anchor 115a and extend vertically. The third thermal shield part 115 may be formed of aluminum or copper. The third thermal shield part 155 may extend to cover the SQUID sensor module 170.

A first superinsulation layer 154 may be disposed between the first thermal shield part 151 and the second thermal shield part 153, and a second superinsulation layer 156 may be disposed between the second thermal shield part 153 and the third thermal shield part 155. The superinsulation layers 154 and 156 may include total 100 folds or more of superinsulators and polyester nets. The superinsulator may block radiant heat influx.

The SQUID sensor module 170 includes a sensor coupling plate 172 formed of a dielectric material, sensor fixing blocks 174 mounted on a bottom surface of the sensor coupling plate 172, and SQUID sensors 176 coupled with the sensor fixing blocks 174. The sensor coupling plate 172 may be disc-shaped and may be formed of G-10 epoxy. The sensor fixing block 174 may be formed of G-10 epoxy and fix the SQUID sensor 176. The SQUID sensor 176 may measure a magnetic signal of a measurement target 20 disposed on a bottom surface of the outer container 120.

The sensor fixing block 174 may be inserted into a groove formed on a bottom surface of the sensor coupling plate 172 to be fixed using an epoxy adhesive. The sensor fixing block 174 may be electrically connected to the SQUID sensor 176 via an electrical connector. Fixing structure 178 such as a dielectric bolt may couple the sensor fixing block 174 and the SQUID sensor 176 with each other. The SQUID sensor 176 may be separated from the sensor fixing block 174 by removing the fixing structure 178. The sensor fixing block 174 may include a printed circuit board (PCB) and an interconnection 163 for electrical connection to the SQUID sensor 176. The interconnection 163 of the sensor fixing block 174 may be connected to an external circuit via a connection port 162 formed on a top plate 102 of the inner container 110.

The heat transfer pillar 141 may be connected to an inner base plate 118 of the inner container 110. The heat transfer pillar 141 may be formed of copper having high heat conductivity. The inner base plate 118 may be formed of a conductive material and may be disc-shaped. Eight heat transfer pillars 141 may be provided. The heat transfer pillars 141 may be cylindrical and may be disposed symmetrically on a constant circumference on the basis of the center of the inner base plate 118.

A fixing block 119 may be disposed at the inner base plate 118 to improve thermal conductivity of the heat transfer pillar 141 and the inner base plate 118. The fixing block 119 may be disposed through the inner base plate 118. One end of the heat transfer pillar 141 may be inserted into the fixing block 119 to be fixed. The fixing block 119 may be in direct contact with a coolant 160 filling the inside of the inner container 110. The fixing block 119 may be welded or sealed with the inner base plate 118 to maintain a vacuum state.

A thermal conduction plate 142 is disposed on the sensor coupling plate 172 to cool the SQUID sensor module 170. The heat conduction plate 142 may be formed of a copper material and may be disc-shaped. Thus, heat flows to the coolant 160 via the SQUID sensor module 170, the heat conduction plate 142, the heat transfer pillar 141, and the fixing block 119.

The magnetic shield part 143 is disposed in the vicinity of the SQUID sensor module 170 to shield thermal noise and magnetic noise generated from a metal. The magnetic shield part 143 may be formed of a superconducting material. The magnetic shield part 143 may be in the form of a cylinder with a lid. The superconducting material may be lead (Pb) or niobium (Nb). The magnetic shield part 143 may be disposed between the heat conduction plate 142 and the sensor coupling plate 172. Since the superconducting material has very high thermal mass, heat is not transferred well to the SQUID sensor 176. Therefore, auxiliary structure for cooling the SQUID sensor 176 is required. The heat conduction plate 143 may cool the magnetic shield part 143 at uniform temperature.

An auxiliary heat transfer layer 148 is disposed to cover the SQUID sensor 172 using a copper mesh having high thermal conductivity. A fixing ring 149 fixes the auxiliary heat transfer layer 148 to a bottom surface of the inner container 110.

The fixing ring 149 may be formed of a conductor such as copper. The fixing ring 149 attaches the end of the auxiliary heat transfer layer 148 to the inner base plate 118 of the inner container 110. Preferably, a surface of wefts and warps of the copper mesh is electrically insulated not to generate induction current. Accordingly, temperature of the inside surrounded by the inner base plate 118 of the inner container 110 and the auxiliary heat transfer layer 149 is in state of thermal equilibrium with temperature of the inner base plate 118 of the inner container 110. Thus, the SQUID sensor 172 and the magnetic shield part 143 may be uniformly cooled. The auxiliary heat transfer layer 149 may be disposed to cover a bottom surface and a side surface of the overall block including the heat transfer pillar 141, the magnetic shield part 143, the heat transfer plate 142, and the SQUID sensor module 170.

According to a modified embodiment of the present disclosure, the auxiliary heat transfer layer 148 may include an epoxy layer and copper conductor lines stacked on the epoxy layer and extending parallel with each other at regular intervals.

Four power lines, two signal lines for transmitting a magnetic signal detected at the SQUID sensor 176 to an external circuit, and two heater lines for removing a flux trap are required to operate a single SQUID sensor 176. The sensor fixing block 174 includes a printed circuit board (PCB) on which an 8-pin-type connector is mounted. A manganin line formed of a Cu—Mn—Ni alloy having low thermal conductivity may connect the PCB and an external connector (not shown) to each other. The external connector is connected to a driving circuit of the SQUID sensor 176.

The SQUID sensor 176 may include a bobbin on which a pick-up coil is wound, a SQUID PCB, and an 8-pin-type connector. The bobbin may be formed of G-10 epoxy and may be cylindrical. The SQUID may be electrically connected to the PCB, and the 8-pin-type connector may be mounted on the PCB. The 8-pin-type connector may be removably coupled with the 8-pin-type connector of the sensor fixing block 174. Thus, the 8-pin-type connector may be removed from or coupled with an 8-pin-type connector of the sensor fixing block 174. Fixing structure 178 such as a non-metal bolt may be coupled with the sensor fixing block 174 via a hole formed at the bobbin.

An insert 180 is inserted into the inner container 110 to supply a coolant to the inner container 110 and block heat transfer by the insert 180. The insert 180 includes an insert top plate 181 lying on the top plate 101 of the inner container 110, at least one guide rod that is fixed to the insert top plate 181 and extends vertically, and at least one insert baffle 182 inserted into the guide rod 180.

The insert top plate 181 may be formed of G-10 epoxy and may be disc-shaped. The insert top plate 181 may be mounted on the top plate 101 of the inner container 110. A coolant guide tube (not shown) may be mounted on the insert top plate 181 to inject a coolant.

The guide rod 184 may be fixed to the insert top plate 181 to extend vertically. The guide rod 184 may be formed of G-10 epoxy. Four guide rods may be provided. The insert baffle 182 may include a Styrofoam 182a and a conductive plate 182b. The Styrofoam 182a may block conductive heat influx. The conductive plate 182b may block radiant heat influx. The conductive plate 182b may include an aluminum-coated Mylar and a copper layer that are stacked in the order named. The insert baffle 180 may block external heat conduction and radiant heat influx.

As described above, an apparatus for indirectly cooling a superconducting quantum interference device (SQUID) according to an embodiment of the present disclosure includes a low-temperature coolant storage container formed of a metal material and uses a superconducting magnetic shield to protect a SQUID sensor from thermal noise and magnetic noise of a metal. Accordingly, when there was no superconducting magnetic shield, a SQUID sensor of 90 percent or higher did not operate and the sensor of 10 percent exhibited an unstable operation.

Meanwhile, when a superconducting magnetic shield was used, the used SQUID sensor normally operated 100 percent. This means that a magnetic shield material used in a system and the SQUID sensor are cooled well to critical temperature or less. Moreover, thermal noise and magnetic noise generated from a low-temperature coolant storage container were shielded using the superconducting magnetic shield. Therefore, it was confirmed that a metal can be used as a material of a low-temperature coolant storage container for measuring biomagnetism. As a result, a material of a low-temperature coolant storage container may be replaced with a metal material without use of G-10 epoxy.

Although the present disclosure has been described in connection with the embodiment of the present disclosure illustrated in the accompanying drawings, it is not limited thereto. It will be apparent to those skilled in the art that various substitutions, modifications and changes may be made without departing from the scope and spirit of the present disclosure.

What is claimed is:

1. An apparatus for indirectly cooling a superconducting quantum interference device (SQUID), comprising:
an outer container extending in a vertical direction;
a metallic inner container inserted into the outer container to store a liquid coolant, the metal inner container including a top plate;
a SQUID sensor module disposed between a bottom surface of the outer container and a bottom surface of the inner container;
a heat transfer pillar adapted to cool the SQUID sensor module, the heat transfer pillar having one end connected to the bottom surface of the inner container and the other end directly or indirectly connected to the SQUID sensor module;
a magnetic shield part formed of a superconductor covering a top surface of the SQUID sensor module; and
a heat conduction plate being in thermal contact with the other end of the heat transfer pillar, the heat conduction plate being stacked on a top surface of the magnetic shield part,
wherein the inner container has a space spaced apart from the outer container and a space between the inner container and the outer container is in a vacuum state.

2. The apparatus as set forth in claim 1, further comprising:
an auxiliary heat transfer layer disposed to a bottom surface of the SQUID sensor module.

3. The apparatus as set forth in claim 2, wherein the auxiliary heat transfer layer is formed of a copper mesh, and wherein wefts and warps of the copper mesh are electrically insulated from each other.

4. The apparatus as set forth in claim 2, wherein the auxiliary heat transfer layer comprises:
an epoxy layer; and
copper conductor lines stacked on the epoxy layer and extending parallel with each other at regular intervals.

5. The apparatus as set forth in claim 2, further comprising:
a fixing ring formed of a conductor to fix the auxiliary heat transfer layer to the bottom surface of the inner container.

6. The apparatus as set forth in claim 1, further comprising:
a fixing block formed of a copper material and fixed to the bottom surface of the inner container to transfer heat to the heat transfer pillar.

7. The apparatus as set forth in claim 1, wherein the outer container comprises:
an upper outer cylinder;
a washer-shaped outer middle plate connected to a bottom surface of the upper outer cylinder;
a lower outer cylinder being in contact with an inner side surface of the outer middle plate to vertically extend; and
an outer base plate disposed on a bottom surface of the lower outer cylinder.

8. The apparatus as set forth in claim 1, wherein the inner container comprises:
a neck portion connected to an inner side surface of a through-hole formed in the center of a top plate, the neck portion extending vertically;
a washer-shaped inner middle plate connected to a bottom surface of the neck portion, the inner middle plate having a through-hole in its center;
a cylindrical inner body portion extending vertically from an outer side surface of the inner middle plate; and
an inner base plate disposed on a bottom surface of the inner body portion.

9. The apparatus as set forth in claim 1, wherein the SQUID sensor module comprises:
a sensor coupling plate formed of a dielectric material;
sensor fixing blocks mounted on a bottom surface of the sensor coupling plate; and
SQUID sensors coupled with the sensor fixing blocks.

10. The apparatus as set forth in claim 1, wherein the magnetic shield part is formed of lead (Pb) or niobium (Nb).

11. The apparatus as set forth in claim 1, wherein the heat conduction plate and the heat transfer pillar are formed of an oxygen-free copper material.

12. The apparatus as set forth in claim 1, wherein the magnetic shield part extends vertically to cover the SQUID sensor module.

13. The apparatus as set forth in claim 1, further comprising:
a first support plate coupled with an outer side surface of the inner container, the first support plate having a first diameter and including a first conductive thermal anchor formed on its outer circumferential surface;
a second support plate spaced vertically apart from the first support plate to be coupled with the outer side surface of the inner container, the second support plate having a second diameter smaller than the first diameter and including a second conductive thermal anchor formed on its outer circumferential surface;

a third support plate spaced vertically apart from the second support plate to be coupled with the outer side surface of the inner container, the second support plate having a third diameter smaller than the second diameter and including a third conductive thermal anchor formed on its outer circumferential surface;

a first thermal shield part coupled with the first thermal anchor and extending vertically;

a second thermal shield part coupled with the second thermal anchor and extending vertically; and a third thermal shield part coupled with the third thermal anchor and extending vertically.

14. A method for indirectly cooling a superconducting quantum interference device (SQUID), comprising:

providing an outer container extending vertically and a metallic inner container inserted into the outer container to store a liquid coolant, the inner container including a top plate and a space between the inner container and the outer container being in a vacuum state;

providing a SQUID sensor module between a bottom surface of the outer container and a bottom surface of the inner container;

providing a heat transfer pillar having one end connected to the bottom surface of the inner container and the other end connected directly or indirectly to the SQUID sensor module to cool the SQUID sensor module;

providing a magnetic shield with a superconductor disposed to cover a portion of the SQUID sensor module; and providing a heat conduction plate being in thermal contract with the other end of the heat transfer pillar and being adapted to cool the superconductor.

15. The method as set forth in claim 14, further comprising:

providing an auxiliary heat transfer layer covering a bottom surface of the SQUID sensor module to cool the heat transfer pillar, the superconductor, and the SQUID sensor module.

* * * * *